(12) United States Patent
Shakespeare (10) Patent No.: US 6,421,575 B1
(45) Date of Patent: Jul. 16, 2002

(54) METHOD AND CONTROL ARRANGEMENT FOR CONTROLLING SHEET-MAKING PROCESS

(75) Inventor: John Shakespeare, Siuro (FI)

(73) Assignee: Metso Paper Automation Oy, Tampere (FI)

(*) Notice: Subject to any disclaimer, the term of this patent is extended or adjusted under 35 U.S.C. 154(b) by 0 days.

(21) Appl. No.: 09/452,397

(22) Filed: Dec. 1, 1999

(51) Int. Cl.⁷ ................................................. G06F 7/66
(52) U.S. Cl. ........................... 700/127; 700/29; 700/38; 162/262; 162/263
(58) Field of Search ................................ 700/127–129, 700/28–34, 36–39; 73/159; 162/253, 262, 263, DIG. 10; 702/189

(56) References Cited

U.S. PATENT DOCUMENTS

| | | | |
|---|---|---|---|
| 4,374,703 A | * | 2/1983 | Lebeau et al. ............... 162/253 |
| 5,539,634 A | | 7/1996 | He .............................. 364/158 |
| 5,877,954 A | * | 3/1999 | Klimasauskas et al. ....... 700/28 |
| 5,893,055 A | | 4/1999 | Chen .......................... 702/189 |
| 6,230,062 B1 | * | 5/2001 | Shah ........................... 700/29 |

OTHER PUBLICATIONS

John Shakespeare and Tarja Shakespeare, An Optimizing Color Controller, *Tappi Journal* Sep. 1998, pp. 171–179, vol. 81, No. 9.

Emmanuel C. Ifeachor and Barrie W. Jervis, Digital Signal Processing, A Practical Approach, Contents, pp. xiii–xxiii; Addison–Wesley Publishing Company, © 1993.

International Search Report, PCT/FI00/01049, completed Mar. 19, 2001.*

* cited by examiner

*Primary Examiner*—Leo Picard
*Assistant Examiner*—Steven R. Garland
(74) *Attorney, Agent, or Firm*—Alston & Bird LLP (57) ABSTRACT

The invention relates to a method and an arrangement for controlling a sheet-making process. In the solution, a sheet matching desired values is manufactured. A measuring unit measures the state of the process to produce one or more measurement value representing the state of the process. A comparator compares each measurement value with a corresponding desired value and, on the basis of the comparison, forms an error representing the difference between at least one measurement value and desired value. A control unit forms at least two control action candidates based on the error using at least two process models, of which at least one is a perturbed process model. A processing unit forms one control action from the control action candidates, with which control action the sheet-making process is controlled to produce a sheet matching the desired values.

32 Claims, 6 Drawing Sheets

METHOD AND CONTROL ARRANGEMENT FOR CONTROLLING SHEET-MAKING PROCESS

FIELD OF THE INVENTION

The invention relates to a method for controlling a sheet-making process and to a control arrangement of the sheet-making process operating according to the method.

BACKGROUND OF THE INVENTION

The quality of a sheet being manufactured is usually measured across the web by cross-directional (CD) and other measurements. Typical variables measured in CD measurements are moisture content, caliper, basis weight, and ash content. Other typical measurements which describe the quality of the sheet are color, opacity, gloss, and smoothness, which may or may not be CD measurements. The measurement results are compared with the set values and an error profile is formed to show the difference between the measurement results and the set values. A process which is in a state matching the set values is known to produce a sheet of a desired quality and, thus, the process should be kept in a state matching the set values as exactly as possible. By means of the error profile and a nominal process model, a controller gives a control command to one or more actuators which alter the process according to the command. The process alteration results in a change in the CD or other properties of the sheet, and this change occurs in the time domain (TD) in a certain way. The nominal process model describes the TD and/or CD and/or other aspects of the process response to the actuator. In paper-making in particular, amount or combinatory proportion of material or mechanical load or heat applied to the sheet during the process can be used as actuators. The measurement variables are altered or maintained by means of the actuators to keep the quality of the paper being made good. For each combination of actuator and measured sheet property, the process model comprises some or all of (i) CD mapping, (ii) CD response, (iii) TD mapping, (iv) TD response, (v) process gain, and may comprise additional aspects as well. One such sheet-making system is described in U.S. Pat. No. 5,539,634, which is incorporated herein by reference. The terms mapping and response are known per se to those skilled in the art of control of sheet properties, but are defined later in this disclosure.

However, there is always some uncertainty in the process model used by a controller. A sophisticated controller may perform very well with an accurate process model, but the disadvantage is that the controller performs badly with an inaccurate model. The deterioration in control performance depends on the nature of the inaccuracy in the model and the sensitivity of the controller to that kind of error.

BRIEF DESCRIPTION OF THE INVENTION

Thus, it is an object of the invention to implement a method and a control arrangement implementing the method in such a manner that the process can also be controlled well with an inaccurate nominal process model. The method and the arrangement therefore comprise a robust controller. This object is achieved by the method for controlling the sheet-making process disclosed in the preamble, in which method a sheet matching the desired values is manufactured, in which method: the state of the process is measured to get one or more measurement values representing the state of the process; each measurement value is compared with a corresponding desired value; on the basis of the comparison an error is formed, representing at least one difference between the measurement value and the desired value; at least two control action candidates based on the error are formed by means of at least two process models, of which at least one is a perturbed process model; one control action is formed from the control action candidates to control the sheet-making process to produce a sheet matching the desired values.

A further object of the invention is a control arrangement for controlling a sheet-making process which is adapted to produce a sheet matching the desired values, which arrangement comprises: a measuring unit for measuring the state of the process, which produces one or more measurement value representing the state of the process; a comparator for comparing each measurement value with the corresponding desired value and for forming an error representing at least one difference between the measurement value and the desired value; a control unit which is adapted to utilize at least two process models, of which at least one is a perturbed process model, the control unit being also adapted to form at least two control action candidates based on the error; a processing unit for forming one control action of the control action candidates, with which control action the control arrangement is adapted to control the sheet-making process to produce a sheet matching the desired values.

Preferred embodiments of the invention are set forth in the dependent claims.

The method and arrangement of the invention provide several advantages. One major advantage is that a robust controller tolerates well errors in the process models and thus, it performs well, even with errors (of limited magnitude) in its process model. The controller performs well because its actions have been formed from a range of process models, which have a higher likelihood of encompassing the true process model than would a single nominal model.

BRIEF DESCRIPTION OF THE DRAWINGS

The invention will now be described in greater detail in connection with preferred embodiments and with reference to the attached drawings, in which.

DETAILED DESCRIPTION OF THE INVENTION

The solution of the invention can be applied especially to a sheet-making process, such as paper and board making and the manufacture of plastic sheets, without, however, being restricted to them.

Let us first examine the processes by means of a simple formulae. The nominal model R of the process can be defined as follows:

$$R = \frac{\partial P}{\partial A},$$

where $\partial P$ is the partial differential variation of the process in relation to the partial differential variation $\partial A$ of the actuator. In general, P is a vector of process values and A is a vector of actuator values, which need not be the same length as P. In this case, R is a matrix whose size is determined by the lengths of P and A. This relation can also be expressed in transform spaces, for example using the Laplace transform P(s) of P, A(s) of A, and R(s) of R, in which the differential operation is replaced by an algebraic operation: R(s)=P(s)/A(s). The method of the invention can be applied in transform spaces as well as in direct calculations, but for clarity is presented here without such transformation. The nominal model of the process, $\hat{R}$, is estimated empirically from earlier measurements, where such estimation may be recursive, or may be estimated from a prior process knowledge such as equipment dimensions and the nature of the physical processes occurring therein. This way, the required actuator difference change $\Delta\hat{A}$ at each moment of time can be calculated by means of the difference deviation $\Delta P$ of measured process conditions and the estimated nominal model $\hat{R}$ as follows:

$$\Delta\hat{A} = \hat{R}^{-1}\Delta P,$$

where $\Delta P$ is $\Delta P = P_h - P_m$, $P_h$ is the desired state of the process, $P_m$ is the measured state of the process and $\hat{R}^{-1}$ is the inverse matrix of the nominal model estimate of the process. $\Delta P$ can also be called an error signal.

Figure 1:
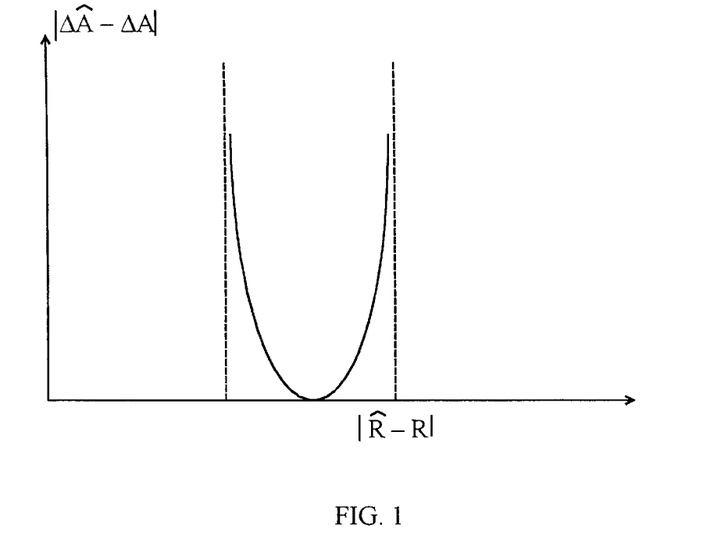
FIG. 1 shows an error in the operation of an actuator as a function of an error in the process model.

FIG. 1 shows an error $|\Delta\hat{A} - \Delta A|$ occurring in the operation of the actuator, where $\Delta\hat{A}$ is the actuator change based on the nominal process model $\hat{R}$ and $\Delta A$ is the actuator change based on the true process model R, as a function of the difference between the nominal process model $\hat{R}$ and the true process model R. The greater the error in the estimated process model in relation to the true process model, the greater the deviation of the actuator operation from the desired operation. Such an error quickly leads to an entirely wrong state of the process and to the deterioration of the quality of the product being made.

Figure 2:
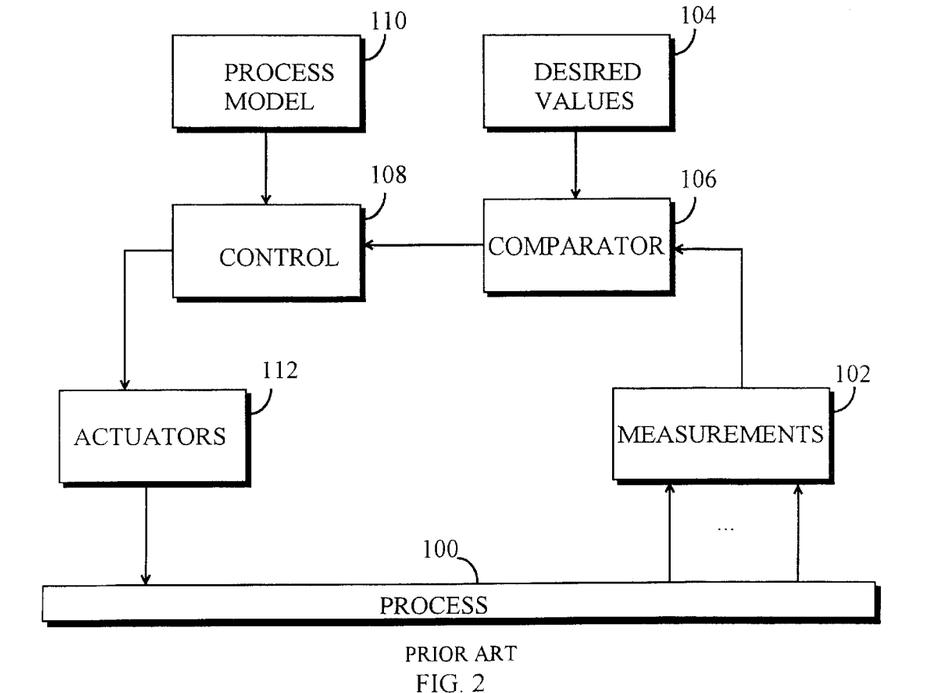
FIG. 2 illustrates process control.

Let us now examine a sheet-making process known per se by means of FIG. 2. The state of the process is measured by measuring the properties of a sheet 100 with N measuring heads in cross-machine direction in a measuring unit 102, where N is a positive integer. Alternatively, a lesser number of measuring heads can traverse the sheet in the cross-machine direction and measurements at N locations across the sheet can be provided from their measurements. The measuring results $P_m$ of the measuring unit 102 and the desired values $P_h$ from block 104 are fed into a comparator 106 which forms an error signal $\Delta P$ of the differences between the desired values and the measured values. A control unit 108 forms a control signal, whose purpose is to produce a required variation $\hat{A}$ in the operation of the actuator, by means of the error signal and the process model $\hat{R}$ received from block 110. The actuators 112, whose quantity is V and V is a positive integer which need not equal N, operate according to the control signal and thus affect the sheet-making process and the quality of the sheet.

Plural actuators 112 are commonly deployed across a sheet-making apparatus in order to regulate one or more properties of the sheet in the cross-machine direction. For example, the plural feed steams to a dilution headbox of a paper machine may be combined in different proportions at each of plural locations across the headbox by means of controllable valves, whereby the properties of the combined feedstuff in the headbox can be manipulated in the cross-machine direction. Similarly, the headbox of a paper machine may have spindles attached to its slice lip at plural locations across the headbox, whereby the shape of the slice aperture can be manipulated in the cross-machine direction, whereby the flow pattern in the headbox discharge can be manipulated. Other cross-machine actuators 112, such as steam boxes, rewet sprays, coater blades, calender rolls, loadable shoes, zone-controlled rolls, and so forth, each having its own plurality of adjustable elements, may be situated in the presses, dryers, coaters, calenders, and other units of a paper manufacturing process.

Other sheet-making or sheet processing processes 100, such as extruders for plastic sheet or film, or laminating or converting equipment, or printing presses, commonly have means of adjustment in the cross-machine direction. These means include extruder bolts, loadable presses, variable nozzles, heaters, moisturizers and tensioners, and perform analogous functions to those described for paper machines.

Sheet properties are commonly measured at a plurality of locations across the sheet, where such plurality normally equals or exceeds the plurality of actuators 112. The set of measurements of a property in the measuring unit 102 across the sheet is commonly referred to as the profile of that property. Profiles may be measured by sensors which traverse across the sheet, or by arrays of sensors at fixed locations across the sheet. Measurements of properties of the sheet are commonly derived from sensors based on nuclear, electromagnetic, thermal, or mechanical mechanisms and they are obvious to those skilled in the art. Properties of interest in paper making are basis weight, moisture content, ash content, caliper, gloss, color, opacity, fiber orientation distribution, tensile strength, smoothness, etc.

The effect of an actuator element on a measured sheet property profile is referred to as the CD response of the actuator. For instance, the change in basis weight caused by moving one slice spindle is the CD basis weight response of the spindle. Each actuator can affect more than one property, so that CD moisture and CD caliper responses may also occur as a result of the spindle movement. The set of CD locations at which responses of the CD actuator elements are centered is referred to as the CD mapping for the actuators 112.

In general, the CD response does not occur instantaneously, but evolves in a particular way over a certain time. This is referred to as its TD response. Moreover, the TD response does not generally commence immediately, but after some process dead-time, as a result of various process delays etc. By analogy with the CD mapping, this delay is referred to as the TD mapping of the actuator.

Let us now examine the background of the invention. A process model has various errors for various properties of parameters and they affect the operation of the process in different ways. The table below summarizes the expected model error, the sensitivity of CD and TD algorithms used in usual controllers and the necessity of robustness. The table is primarily for CD control of a dilution headbox, but other CD processes would be similar.

| | Expected Model Error | Sensitivity of CD Optimizer | Sensitivity of TD Algorithm | Necessity of Robustness |
|---|---|---|---|---|
| CD Mapping | large | high | low | high |
| CD Response | medium | medium | low | medium |
| TD Mapping | medium | medium | medium | medium |
| TD Response | medium | low | low | low |
| Process Gain | medium | low | low | low |

For control of non-CD processes, of course, there is no CD response or CD mapping and hence no sensitivity to CD mapping or CD response errors. However, other aspects of the nominal process model may exist in addition to or instead of the CD aspects, and there will be a need for some level of robustness with respect to errors in those aspects of the nominal process model. In general, processes always have TD responses and mapping, and some processes exhibit high sensitivity to errors in TD mapping.

Since the sensitivity of CD controllers to CD mapping errors is high, and significant uncertainty exists with regard to mapping, it is beneficial to provide robustness with respect to CD mapping. Sensitivity with respect to response shape is lower, provided sampling artifacts are avoided. For a controller which employs a dead-time compensator, sensitivity to errors in dead-time (TD mapping) can be high. Sensitivity to errors in transient (TD response) is lower. For a steady-state controller, the sensitivity to errors in time domain is low. Sensitivity to errors in process gain is low, and relatively large process gain errors can be accommodated. Typical upper bounds are

| | |
|---|---|
| CD mapping | ±0.25 * actuator zone width |
| CD response | ±0.1 * model response width |
| TD mapping | ±1.0 * control execution interval |
| TD response | ±2.0 * control execution interval |
| Process grain | ±0.2 * model process grain |

Figure 3:
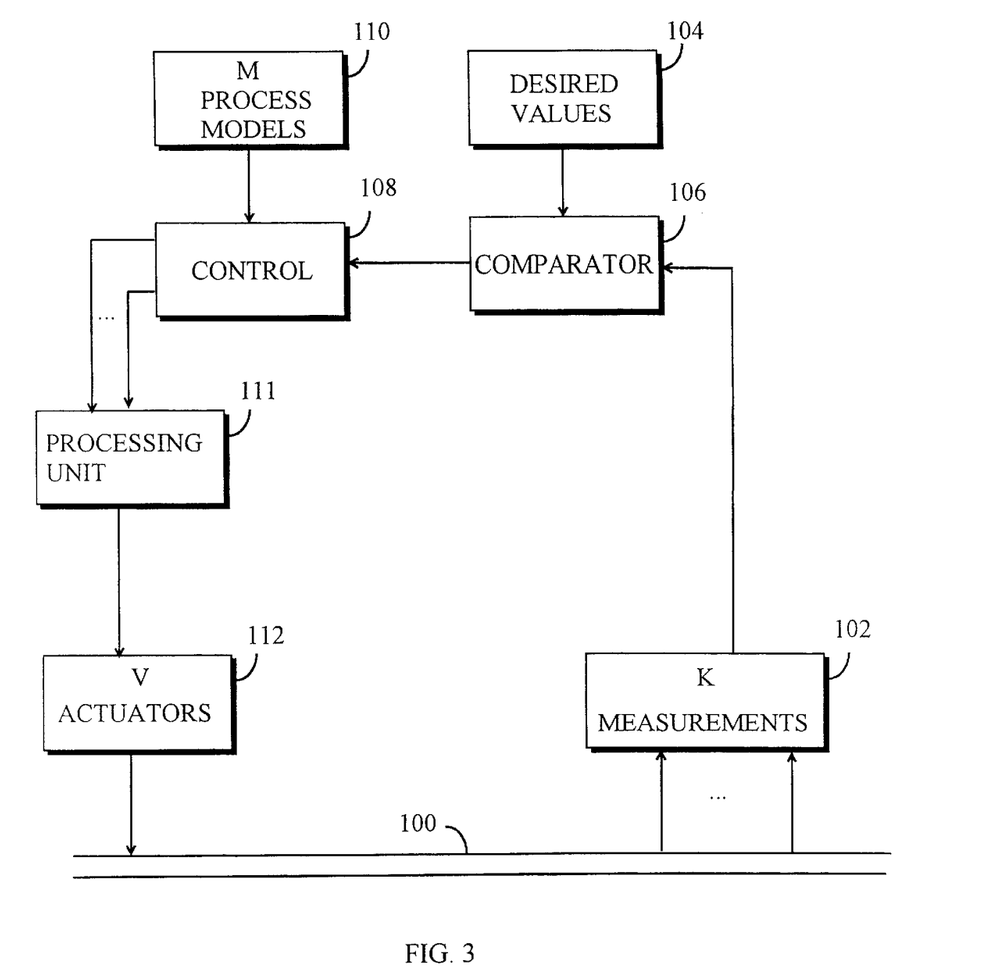
FIG. 3 illustrates process control using several process models.

Let us now examine the method of the invention on a general level using FIG. 3. The sheet 100 is measured in the same way as in block 102 in FIG. 2. As in the case in FIG. 2, the measurement results and the desired values obtained in the measuring unit 104 are compared in the comparator 106 and an error signal is formed. An important part with respect to the invention starts after this. A set of process models is constructed as perturbations of the nominal process model in block 110. The set of process models can be preconstructed and stored in the block 110. Whether the set of process models is formed in block 110 or is formed dynamically in block 110 or whether it is stored in block 110, too, is not significant with respect to the invention. What is significant is that the set of process models are available for the control unit 108. The controller unit 108 executes each of these process models, of which at least one is a perturbed process model, and calculates a control action candidate for each.

The control unit 108 operates in a process modelled by a mapping and a response, for instance, as follows. For each combination of perturbed mapping $map_j$ and perturbed response $resp_j$, a control action candidate is calculated in a manner known per se from the error profile using for example an optimizer:

$$action_j = optim(map_j, resp_j, error), J=1, \ldots, m$$

where $map_j$, $resp_j$, error represent the process model and error of at least one profile, and $action_j$ is the control action candidate. The perturbed response can contain gain perturbations as well as response shape perturbations. An optimizer normally calculates the control action candidate which minimizes the 2-norm or infinity-norm of the error profile. However, other objectives can be included in the optimization, using weighting factors to combine the various objectives into an overall optimization objective. For example, the 2-norm or infinity-norm of the control action, or of derivatives of the control action or actuator, or other functionals based on the error profile or actuator profile can also be minimized. In this example, the control action candidates were calculated by an optimizer, but other calculation techniques can be used instead, employing for example neural networks or fuzzy logic with a variety of possible control objectives. One way of forming the control action candidates is to have a single controller calculate the control action candidates sequentially for each process model. Another way to form the control action candidates is to have the control unit comprise controller blocks and each controller block calculates one control action candidate. In this way, different control algorithms can be used with the the variant process models. This is especially useful if the variant process models differ in model structure or complexity, rather than merely differing in the value of model parameters with a common model structure. Different model structures can arise, for example, if a process is described as a Fourier domain CD model, and also using a CD model employing projection onto othogonal polynomials or some other basis, so that parameters for one model structure are not necessarily meaningful for another model structure. The set of control action candidates ($action_1$, $action_2$, ..., $action_m$) is reduced to a single composite action in a processing unit 111:

$$control\ action = composite(action_1, action_2, \ldots, action_m)$$

this control action is fed to actuators 112.

Let us next examine more closely the method of the invention. Two or more variant process models, comprising at least one perturbed process model and optionally comprising a nominal model, are supplied to and stored by the robust CD controller. Alternatively, a nominal model and estimates of the uncertainty (or upper bound on expected error) in one or more parameters of the model are supplied to the robust CD controller. In the latter case, the robust controller constructs at least two variant process models by perturbing the nominal model, such that at least one variant is a perturbed model and optionally one variant is the nominal model. A robust controller is a controller whose performance degrades gradually with a range of errors in its process model, and which can provide a guaranteed level of performance in the presence of certain types of error of up to specified magnitudes in the model.

The magnitude of perturbation is calculated from the supplied property or parameter uncertainties. Each variant model can be perturbed in just a single parameter, or in a combination of parameters. Each perturbed parameter can be perturbed by a single amount, or by several different amounts. The set of perturbation amounts for each parameter and the combinations of perturbation amounts in different parameters in each variant model can be automatically calculated by the robust CD controller, or can be generated according to a specified variation pattern supplied to the robust CD controller. Not all variant models need have the same model structure, and models of different structure need not have the same set of parameters. Obviously, variant models can only be perturbed in parameters which they comprise. This procedure generates a set of tentative process models that may include the nominal process model.

For each of these tentative process models, the robust controller calculates a non-robust control action profile for the supplied error profile(s). This procedure results in a set of control action candidate profiles. A robust control action profile is formed as a composite of consensus of the set of control action candidate profiles. Several types of robustness are possible for CD controls: robustness with respect to errors in CD response, CD mapping, TD response, TD mapping, or process gain. Since the sensitivity of CD controllers to CD mapping errors is high, and significant uncertainty exists with regard to mapping, it is beneficial to provide robustness with respect to CD mapping alone.

Figure 4A:
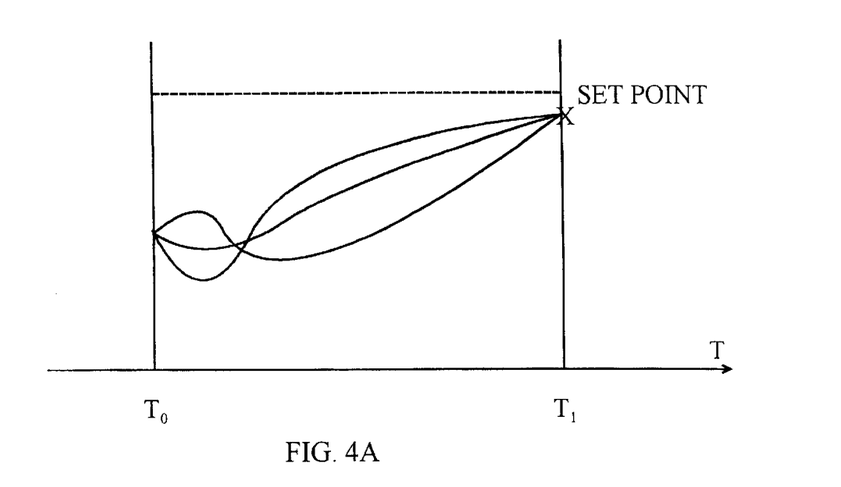
FIGS. 4A–4C shows the behavior of a process with various control actions.
Figure 4B:
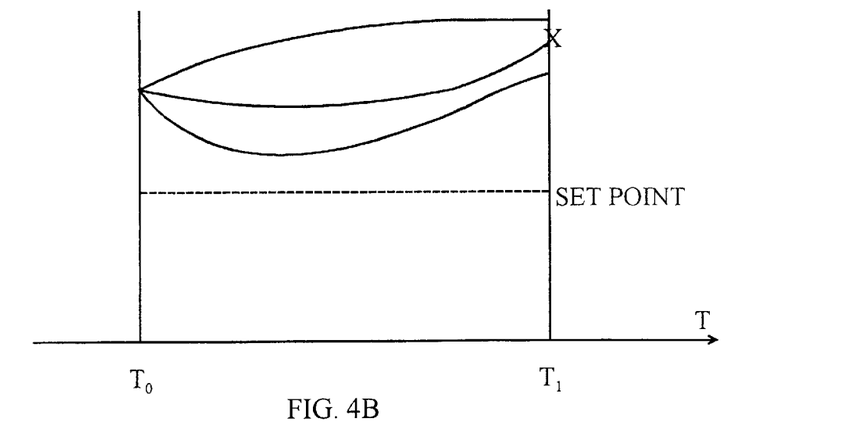
Figure 4C:
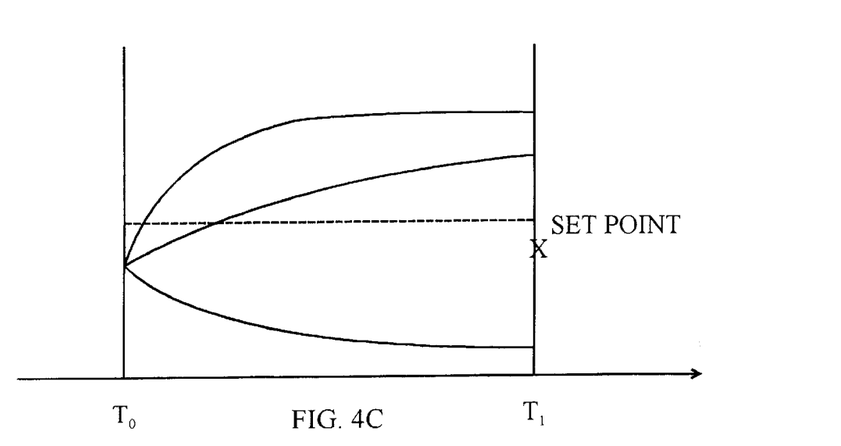

FIGS. 4A to 4C show various estimate curves on the behavior of the process after the starting time $T_0$, when the process is controlled with three different control action candidates. Each estimate is based on different process models used by the controller. A horizontal dashed line shows the set point value. A cross is the average of various state alternatives at the time instant $T_1$. Calculating an average of the different alternatives sometimes leads to a good control, but does not necessarily lead to a good control. In the case of FIG. 4A, all three different control actions lead to the same process state at $T_1$. At this point, any control action formed by the processing unit directs the process to the state according to the estimate. In the case of FIG. 4B, the process states caused by different control action candidates are in the same direction but at different distances from the set point at $T_1$. The average of various control action candidates also leads to a point quite far from the set point. In FIG. 4C, the process states caused by different control action candidates are at $T_1$ far away from each other and at different sides of the set point. Although the average of the various control action candidates is not far from the set point, the individual action candidates are in opposite directions. Thus, one control action to control the sheet-making process is formed using a simple average of the control action candidates.

This situation can be further improved by using a more efficient control action forming than averaging. How the control action is formed is not essential as long as there is a known interdependence between the formed control action and the formed control action candidates. The control action can be selected from the control action candidates or it can be formed from the control action candidates as a combination, consensus, compromise, average, function or the like. Known filtering methods can be used in forming the control action, by treating the set of control action candidates as a set of samples of a signal or a set of samples of a multivariate signal. The control action candidates may be ordered sequentially in a specified way for treatment as samples of a signal, and this ordering need not be the same on each controller execution, or may be ordered in a random or pseudo-random way.

A number of composition methods can be outlined, using formulae which are similar to known filtering methods for digital signal processing found in standard texts, such as Ifeachor & Jarvis, Digital Signal Processing, Addison Wesley, but applied to a discrete set rather than to samples from a continuum.

Another way to form a composite control action is to use weighted averaging of the control action candidates:

$$\text{composite action} = \sum_{j=1}^{m} weight_j action_j \qquad (1)$$

where $weight_j$ is a weighting factor. The weighting factors usually sum to unity. Ideally, each weight factor should be the relative probability that the associated variant model describes the process. In practice, these probabilities are usually not known, but approximations may be available.

Another simple method of composition is to select the control action candidate which has minimum 2-norm or minimum infinity-norm. In other words, to select the control action candidate for which the sum of squares of elements is least, or to select the control action candidate for which the maximum absolute value of any element is least.

A generalization of this method is to use a biased norm, thus selecting the control action candidate whose distance from a reference action is minimum. In other words, to select the control action candidate for which the 2-norm or infinity-norm of its difference from a reference action is least. The reference action can be zero (producing the simple method), or can be supplied by external logic. For example, the reference action can be the action which would move the actuators to a safe state or to a minimum cost state.

One especially efficient way of forming a composite control action is as follows. A rule-based composition method makes the process operate with overdamping. It is disclosed herein as a composition method for profile control actions, but can obviously also be applied to other multivariate control actions or to univariate control actions.

For a set of m control action candidates $action_j$, and given a reference control action ref, a composite control action is formed by the following three rules:

Rule 1:

If $\bigcap_{j=1}^{j=m} \langle action_j > ref \rangle$ is true, then $$\text{composite action} = ref + \min_{j=1}^{j=m} \{action_j - ref\}$$

Rule 1 states that, if all m control action candidates exceed the reference action, then the composite action exceeds the reference action by the minimum excess of the action candidates above the reference action.

Rule 2:

If $\bigcap_{j=1}^{j=m} \langle action_j < ref \rangle$ is true, then $$\text{composite action} = ref - \min_{j=1}^{j=m} \{ref - action_j\}$$

Rule 2 states that, if all m control action candidates are less than the reference action, then the composite action is less than the reference action by the minimum deficit of the action candidates below that reference action.

Rule 3: If neither Rule 1 or Rule 2 was activated, then composite action=ref

Rule 3 states that, if the set of control action candidates do not meet the conditions for activating either rule 1 or rule 2, then the composite action is the reference action.

Clearly, rule 1 and rule 2 are mutually exclusive, and rule 3 is their mutual complement. Thus, the three rules are never in conflict, and cover all possible scenarios. The various operations of these rules (comparisons, additions, subtractions, assignment) are implemented as element by element operations, where each of the V elements of the composite action is derived from the rules independently of the other elements. A control action calculated from plural control action candidates according to these three rules is termed a consensus action.

Normally, the reference action is zero in all of its elements. However, some or all of its elements may be nonzero, and may be supplied by external logic. For example, an control intervention algorithm may attempt to bias the controller output to react to extraneous events. As another example, the reference action may be the action which returns the actuators to a minimum cost state such as the state in which consumption of energy or material is minimum.

Alternatively, the control action candidate calculated using the nominal process model may be used as the reference action. In this case, only the control action candidates calculated using perturbed process models are subjected to the above rules.

Figure 5A:
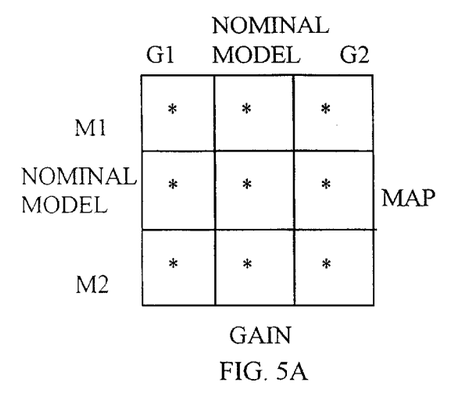
FIG. 5A shows the forming of common control action candidates for a gain process and a map process.
Figure 5B:
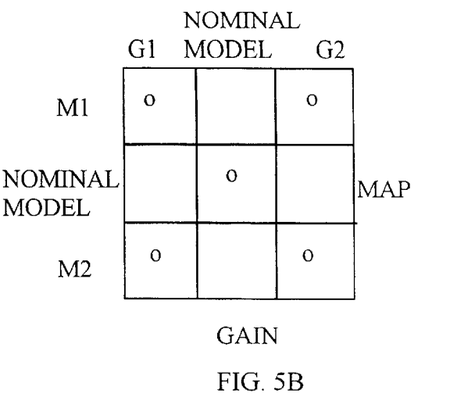
FIG. 5B shows the forming of common control action candidates
Figure 5C:
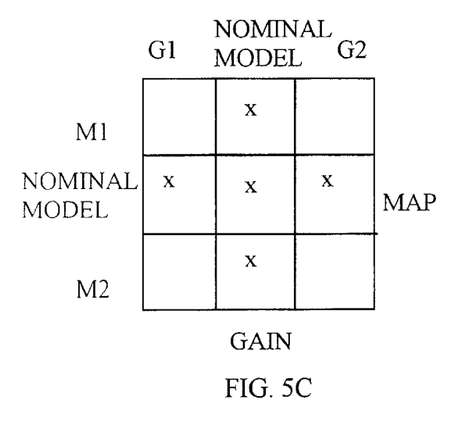
FIG. 5C shows the forming of common control action candidates for a gain process and a map process, for a gain process and a map process.
Figure 5D:
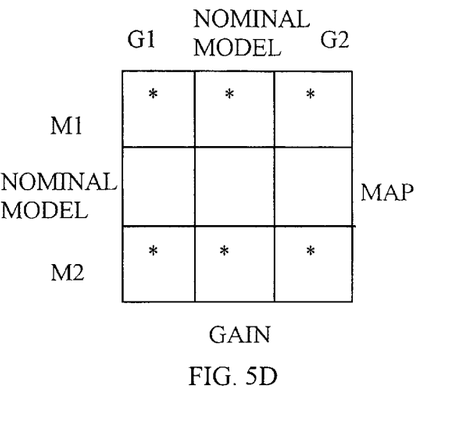
FIG. 5D shows the forming of common control action candidates for a gain process and a map process.

FIGS. 5A to 5D show some exemplary methods for forming sets of variant models incorporating perturbations to two parameters, mapping and gain. Three parameter variations are used for mapping: the nominal mapping and two perturbed mappings M1 and M2. Three parameter variations are also used for gain: the nominal gain and two perturbed gains G1 and G2. In FIG. 5A, all permutations of these parameter variations are used, resulting in a set of nine variant models, including the nominal model. In FIG. 5B, there are five variant models, comprising the nominal model and four perturbed models in which both parameters have been perturbed simultaneously. In FIG. 5C, there are also five variant models, comprising the nominal model and four perturbed models in each of which only one parameter has been perturbed. In FIG. 5D, there are size variant models, none of which is the nominal model. Two of the variant models in FIG. 5D combine the nominal gain with perturbed mappings, while the other four combine perturbations in both parameters simultaneously. In general, if there are W parameters subject to perturbation, and if the nominal state and two perturbations (such as an increase and a decrease compared to the nominal state) are used for each parameter, then the total number of possible variant models is $3^W$. This is the case in FIG. 5A, where W=2, and there are consequently nine variant models. In general, the total number of possible variant models is the product of the number of variant states for each of the parameters subject to perturbation. In other words, if each parameter $parm_i$ has $K_i$ variant states (which may include its nominal state), then the total number of possible variant models is $$\prod_{i=1}^{W} K_i.$$

Clearly, if W is large, or if any of the $K_i$ is large, this can result in a very large number of possible variant models. If more than one model structure is used, then the total number of possible models depends on the number of parameters subject to perturbation in each model structure, and the number of variant states for each such parameter.

The number of variant models in the set employed by the robust controller, and hence the number of control action candidates can, however, be reduced. In general, it is not necessary to employ all of the possible variant models as in FIG. 5A. A subset of the set of possible variant models will usually suffice for provision of robustness, and often a sparse subset will suffice when there are many parameters or many possible states for some parameters. For example, if each of W parameters has a nominal state and two perturbed states, and parameter perturbations are not combined, then 2W+1 variant models (including the nominal model) will result, as is the case in FIG. 5C. The situation depicted in FIG. 5B is similar, except that parameters are perturbed in linearly independent combinations, also resulting in 2W+1 variant models in use. FIGS. 5B and 5C thus illustrate two simple strategies for sampling the set of possible variant models. Many other strategies are possible, depending on the degree of interation between effects of perturbations to different parameters. FIG. 5D, for example, illustrates a different subset, in which all variant models which contain the nominal state for the mapping have been omitted.

The subset of all possible variant models can be specified as a sampling pattern or sampling algorithm. If more than one model structure is used, the sampling method need not be the same for all model structures. If there is a priori knowledge regarding the effects of interactions between perturbations to different parameters, then the sampling pattern can be specified in advance. For instance, the parameters can be perturbed individually, as in FIG. 5C, or in specific combinations, as in FIG. 5B. If parameters are perturbed in combination, the combinations need not be linearly independent. If the effects of interactions between perturbations to different parameters depend on the current state of the process being controller (or equivalently, on the current nominal process model), then the sampling can be specified as an algorithm, if there is no such a priori knowledge, then a random sampling can be used, which need not be the same on each control execution.

A random sampling may conform to a specified statistical distribution. For example, a uniform probability density may be used over the whole set of all possible perturbations, or it may have different densities over some parameters. Alternatively, the random sampling may use the probability density of a multivariate normal or other commonly known statistical distribution. Obviously, each particular set of parameters should appear at most once in the set of variant models in use, so the sampling is performed without replacement.

Figure 6A:
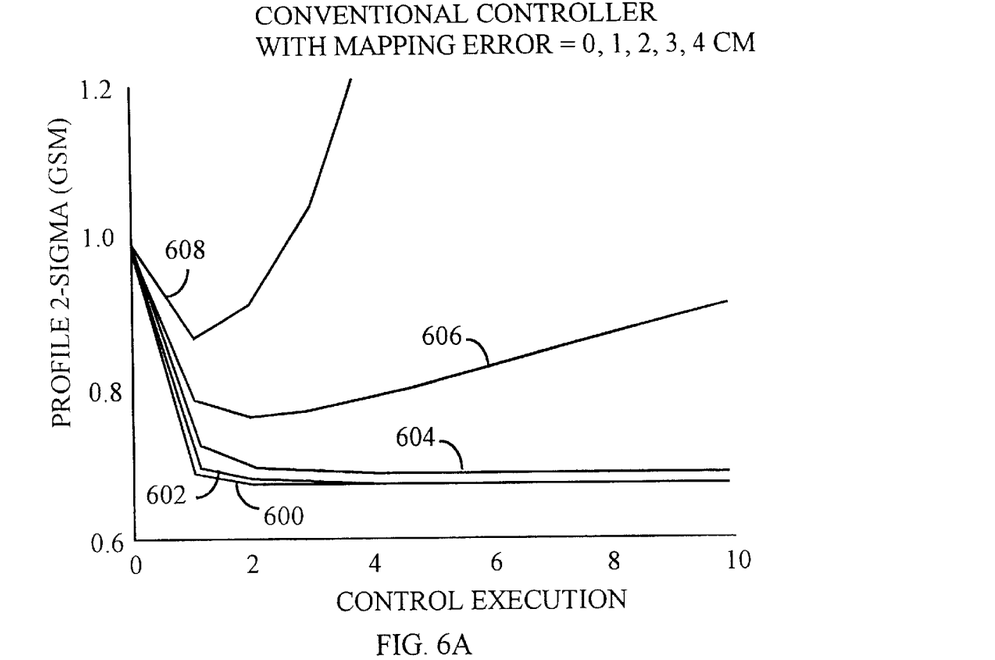
FIG. 6A shows the behavior of a process with non-robust control, for different levels of error in the nominal model.

FIG. 6A shows the simulated performance of a conventional minimum variance CD controller which uses a least-squares optimization to minimize the variance, and hence the standard deviation of the error $\Delta P$. The CD actuator has 70 elements, each 6 cm in width, while the error has 421 elements, each an average of a 1 cm width part of the sheet. For clarity, only the CD part of the control algorithm is considered, and the process is assumed to reach steady-state rapidly in TD. The nominal process model consists of a nominal CD response and a nominal CD mapping, which are combined into a response matrix $\hat{R}$ which has 421 rows and 70 columns. Each column of $\hat{R}$ contains the nominal response of a single actuator in the whole error, with its response centered at the row representing the nominal mapping location for that actuator in the profile. Equivalently, each row of $\hat{R}$ indicates the nominal degree of influence of each of the actuators over a single element in the error. The optimal control action $\Delta A$ which minimizes the variance is thus formed as:

$$\Delta \hat{A} = [\hat{R}^T \hat{R}]^{-1} \hat{R}^T \Delta P$$

FIG. 6A shows how the standard deviation of the error is changed by ten successive executions of this standard minimum variance CD controller from an initial value slightly less than one, where the process has fully responded to each action before the next action is calculated. The bottom line 600 shows the performance when the nominal process model $\hat{R}$ matches exactly the true process model. Its asymptotic value (after further control executions) is 0.6713. The next two lines 602, 604 from the bottom respectively show the performance when the nominal mapping is in error by 1 cm and 2 cm with respect to the true process mapping (so that the nominal response is shifted in CD by 1 cm and 2 cm respectively with respect to the true process response). Although slightly degraded with respect to performance with an exact model of the process, their overall performance is still very good, with asymptotic values of 0.6743 and 0.6872 respectively. The next line 606 shows the performance with an error of 3 cm in the nominal mapping. In this case, although the first two control actions produce an improvement, the controller then causes the process to deteriorate steadily. The uppermost line 608 shows the performance with an error of 4 cm in the nominal mapping. The first control action produces a slight improvement, but thereafter, there is a rapid and continued deterioration, so that after three actions it is worse than its initial state and degrading at an accellerating rate. In the latter two cases (mapping error of 3 cm and 4 cm), the controller has become unstable, and the error variance increases without bound (in practice, a process constraint would impose a bound at some high value). In the first three cases, the controller is stable and performing acceptably. From this, we summarize that this particular minimum variance controller has an innate robustness with respect to mapping errors of about 2 cm when controlling this particular process.

The actuator response and initial profile used in this simulation are taken from a real paper machine, but the mapping was slightly simplified for purposes of clarity. In practice, the nominal model is never exact, and mapping errors exist for many or even all of the actuators. However, the mapping errors are not equal across the profile, and are time varying. Often, local mapping errors exceed 2 cm from time to time. Sometimes, many actuators will have mapping errors larger than 2 cm, especially when the process is ramping between steady operating states. This is typical for real processes, where the sheet width may exceed 1000 cm, the number of actuators may exceed 300, and it is difficult and costly to repeatedly identify the mapping to within 2 cm for every actuator. Note that the plots and numerical results are for twice the standard deviation, rather than for standard deviation or variance. This is a common practice for expressing the amount of CD variation in a profile.

Figure 6B:
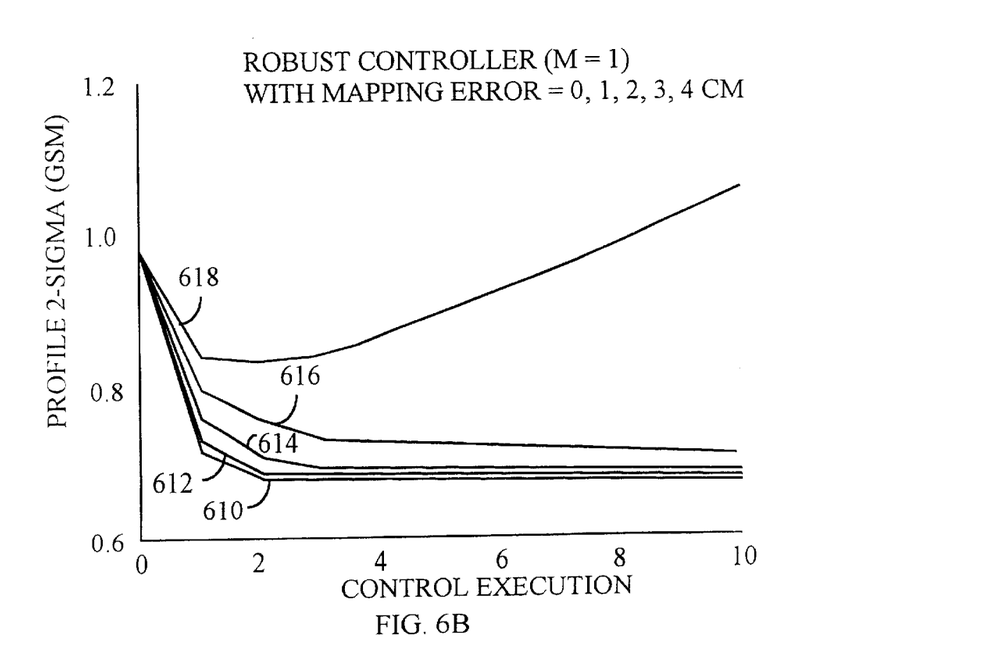
FIG. 6B shows the behavior of a process with robust control employing a moderate degree of robustness, for different levels of error in the nominal model.

FIG. 6B shows the simulated performance of the same minimum variance control algorithm, modified according to the present invention. The simulation uses the same response and mapping data, so that the nominal model $\hat{R}$ is identical, and uses the same initial error $\Delta P$. In this case, perturbations of ±1 cm in the mapping are used to derive two perturbed models, whose response matrices can be represented as $\hat{R}+\delta R_1$ and $\hat{R}+\delta R_2$. Perturbations are made only to the nominal mapping, not to the nominal response. Thus, three control action candidates are formed from the error $\Delta P$ in each control execution, $\Delta \hat{A}_0$ using the nominal process model, and $\Delta \hat{A}_1$ and $\Delta \hat{A}_2$ using the two perturbed process models:

$$\Delta \hat{A}_0 = [\hat{R}^T \hat{R}]^{-1} \hat{R}^T \Delta P$$

$$\Delta \hat{A}_1 = [(\hat{R}+\delta R_1)^T (\hat{R}+\delta R_1)]^{-1} (\hat{R}+\delta R_1)^T \Delta P$$

$$\Delta \hat{A}_2 = [(\hat{R}+\delta R_2)^T (\hat{R}+\delta R_2)]^{-1} (\hat{R}+\delta R_2)^T \Delta P$$

A composite action is then formed from these action candidates. For this example, the method of composition uses the three rules described above, in which the reference action has all elements equal to zero, thus forming a consensus action from the three control action candidates.

FIG. 6B shows how the standard deviation of the error is changed by successive executions of this robust minimum variance CD controller from an initial value slightly less than one, where the process has fully responded to each action before the next action is calculated. The bottom line 610 shows the performance when the nominal process model $\hat{R}$ matches exactly the true process model. Its asymptotic value is 0.6776. The next three lines 612, 614, 616 from the bottom respectively show the performance when the nominal mapping is in error by 1 cm, 2 cm, and 3 cm with respect to the true process mapping. Although slightly degraded with respect to performance of the standard minimum variance controller with an exact model of the process, with asymptotic value of 0.6793, 0.6858, and 0.7077 respectively. The overall performance in these four cases is still very good. In particular, the system is stable and performing quite well with a mapping error of 3 cm, which destabilized the conventional controller. The uppermost line 618 shows the performance with an error of 4 cm in the nominal mapping. The first two control actions produces a slight improvement, but thereafter, there is a gradual deterioration towards an asymptotic value of 17.65. Thus, although it is stable, its performance is bad with a 4 cm error. We conclude that the robust controller with parameter variations of 1 cm in the mapping is more robust than the conventional controller by about 1 cm with respect to mapping errors.

Figure 6C:
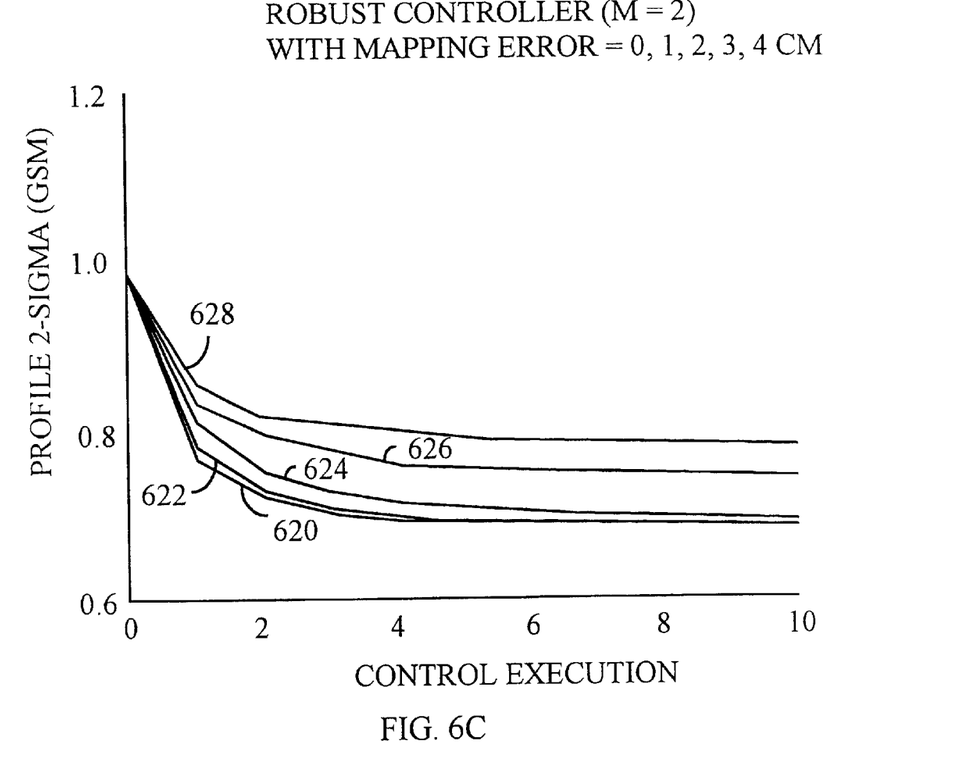
FIG. 6C shows the behavior of a process with robust control employing a high degree of robustness, for different levels of error in the nominal model.

FIG. 6C shows the simulated performance of the same robust minimum variance control algorithm as was used in FIG. 6B, and using the same process data and nominal process model. However, in this case, perturbations of ±2 cm in the mapping are used to derive the two perturbed models. The operation is otherwise identical to that of the controller in FIG. 6B.

FIG. 6C shows how the standard deviation of the error is changed by successive executions of this robust minimum variance CD controller from an initial value slightly less than one, where the process has fully responded to each action before the next action is calculated. The bottom line 620 shows the performance when the nominal process model $\hat{R}$ matches exactly the true process model. Its asymptotic value is 0.6894. The next two lines 622, 624 from the bottom respectively show the performance when the nominal mapping is in error by 1 cm and 2 cm with respect to the true process mapping (so that the nominal response is shifted in CD by 1 cm and 2 cm respectively with respect to the true process response). The asymptotic values are 0.6906 and 0.6933 respectively. There is a slight degradation with respect to performance of the standard minimum variance controller using an exact model of the process, but the overall performance in these three cases is still very good. The next line 626 shows the performance with an error of 3 cm in the nominal mapping. Although there is a degradation in performance, the control is stable and most of the potential improvement is achieved, with an asymptotic value of 0.7055 for 2*sigma. The uppermost line 628 shows the performance with an error of 4 cm in the nominal mapping. In this case, the control is stable, with an asymptotic value of 0.7243. Note that the system is stable and performing quite well with a mapping error of up to 4 cm, which rapidly destabilized the conventional controller. We conclude that the robust controller with parameter variations of 2 cm in the mapping is more robust than the conventional controller by about 2 cm with respect to mapping errors.

Controller performance is commonly expressed as a Harris-type index. We can define such an index here as one hundred times the ratio of the simulated performance of minimum variance control using an exact process model to the simulated performance of each controller using its process model. The ideal index value is 100, and smaller values represent worse performance, so that complete instability has an index of zero. The results of the simulations in FIGS. 6A, 6B, 6C can be summarized in the following table:

| error in nominal mapping | 0 cm | 1 cm | 2 cm | 3 cm | 4 cm |
|---|---|---|---|---|---|
| Standard Controller nominal mapping | 100 | 99.55 | 97.68 | 0.0 | 0.0 |
| Robust Controller, nominal mapping ±1 cm | | 99.07 | 98.82 | 97.89 | 94.86 | 3.80 |
| Robust Controller, nominal mapping ±2 cm | | 97.37 | 97.21 | 96.83 | 95.15 | 92.68 |

Thus we see immediately the benefit of the present invention. At very little cost in performance under modest model errors, the robust controller is stable with higher levels of model error. Furthermore, it provides nearly the same performance under high model errors as under low model errors. Moreover, its increment in robustness compared to the non-robust controller is given by the amount of the perturbation used in its variant models.

Note that the ideal situation, with mapping error equal to zero, rarely or never occurs in practice.

Let us now briefly examine the actuators used in the sheet-making process. Actuators are commonly deployed in the preparation of the feedstuff fed into the sheet manufacturing process. For example, the combinatory proportions of different raw materials, may be varied to achieve desired properties of the sheet. In paper manufacturing, the proportions of hardwood or softwood pulps, or amount of resins or clays may be varied to achieve desired mechanical or compositional properties of the sheet, such as smoothness or ash content. Similarly, additives such as dyes or pigments may be dosed into the feed streams to affect the color or opacity of the manufactured sheet.

Optical and compositional properties are commonly measured using spectroscopic sensors, such as absorption or reflectance or emission or fluorescence spectra in X-ray, ultra-violet, visible, infra-red, or microwave bands or a combination of such means. These measurements may be made at a single location in the cross-machine direction, providing a measurement which is presumed to characterize the whole width of the sheet. Alternatively, the spectral measurements may be made at plural locations across the sheet, providing a profile of spectra, or combined into an average spectrum for the amount of the sheet sampled by the sensors.

Spectroscopic and spectrophotometric measurements are characterized in that they are measurements made at each of plural wavelength bands, and thus are termed wavelength domain (WD) measurements. Thus, any property which is directly measured as a spectroscopic spectrum is a WD measurement. Since properties such as reflectance or transmittance which are measured as WD measurements can also change in the time domain, or can be measured as profiles of spectra, they can also have TD and CD aspects.

Also, any property which is measured indirectly from one or more spectroscopic measurements without necessarily being expressed as a spectrum is a WD property in the context of this invention. For example, color is a WD property which is measured indirectly from spectroscopic measurements of reflectance in the visible range, and which can be expressed in any of several non-spectral coordinate systems, such as CIELAB or tristimulus. Similarly, composition measurements derived from infra-red absorption spectra or from X-ray fluorescence spectra are also WD properties, although they are usually expressed as a mass fraction. Techniques of spectrophotometric colorimetry and spectroscopic quantitative analysis are well known per se, and not further described herein.

The effect of an actuator on the spectroscopic measurement is referred to as the WD response of the actuator, For example, by increasing the amount of red dye in the feedstuff, the reflectance of the sheet in the blue, green, and yellow wavelength ranges are diminished, and the color of the sheet becomes redder. The shape of the change in reflectance is the WD reflectance response of the red dye.

Just as there can be uncertainty in the TD or CD models of a process in which a profile is controlled, there can be uncertainty in the WD model of a process in which a WD property is controlled. In the control of color in papermaking, for example, one or more colorants such as dyes or pigments are dosed into the feedstock from which the paper is formed. The WD response to colorants in the absorption or scattering spectra of the paper changes according to variations in the properties of the substrate. For example, the shape and amplitude of the response to a pigment in the scattering spectrum depends on the geometry of the fibres (diameter, roughness, etc.) and the amount of filler material (kaolin, chalk, precipitated $CaCO_3$, $TiO_2$, etc.) present in the sheet. It can also depend on the temperature and chemical environment (pH, presence of anions and cations) at the dosing point. In some cases, a spectroscopic response shape is not appreciably in error, but it is shifted in wavelength, analogous to a mapping error in a profile.

The present invention can advantageously be applied, therefore, to control of WD properties such as color and composition. A color controller employing WD measurements and a WD nominal process model is described in Shakespeare & Shakespeare, An optimizing Color Controller, TAPPI Journal 81(9) 171–179. September 1998. By employing at least two variant process models, of which at least one is a perturbation of the nominal process model, a WD controller can be made more robust with respect to errors in its nominal process model. For WD controllers, perturbations of the nominal process model can be constructed using one or more perturbations in one or more parameters of the WD process model.

Obviously, the inventive idea which is described primarily for control using process models with CD aspects can equally be applied to control using process models with WD aspects, whether a CD aspect exists or not. By substitution of spectra for profiles, an equivalence exists between WD and CD control problems. While the examples and claims are stated primarily for robustness in CD control, they should also be construed as encompassing robustness in WD control.

CD and WD processes are particular instances of multivariable processes. Hence, by substitution of vectors of measurements for profiles, an equivalence exists between a general multivariable control and CD control problems. Although the example of mapping is not relevent in this case, the structure of the process can still be expressed in the same matrix form as a CD process, and robustness of a multivariable controller can be improved by incorporating variations in the process model according to the present invention. While the examples and claims are stated primarily for robustness in CD control, they should also be construed as encompassing robustness in a general multivariable control.

Moreover, robustness can be combined between WD and TD aspects of control, or between WD and CD aspects of control, or between CD and TD aspects of control, or between CD, TD, and WD aspects of control. The application of the present invention to these combinations will be obvious to those with normal skill in the art of CD or TD or WD control, and such applications are contemplated by and within the scope of the present invention.

Even though the invention has above been described with reference to the example in the attached drawings, it is obvious that the invention is not limited to it, but can be modified in many ways within the scope of the inventive idea disclosed in the attached claims.

What is claimed is:

1. A method for controlling a sheet-making process, wherein a sheet matching desired values is manufactured:
    the state of the process is measured to produce one or more measurement value representing the state of the process;
    each measurement value is compared with a corresponding desired value;
    on the basis of the comparison, an error is formed representing the difference between at least one measurement value and its desired value;
    at least two control action candidates based on the error are formed by means of at least two process models, of which at least one is a perturbed process model;
    one control action is formed from the control action candidates to control the sheet-making process to produce a sheet matching the desired values.

2. A method as claimed in claim 1, wherein the control action is formed using rule-based composition of control action candidates.

3. A method as claimed in claim 2, wherein the rule-based composition employs the following three rules:
    rule 1: if all control action candidates for an actuator exceed a supplied reference action value for the actuator, then a composite action value for the actuator exceeds the reference action value by the minimum excess of the control action candidates above the reference action value;
    rule 2: if all control action candidates for an actuator are less than a supplied reference value for the actuator, then the composite action value for the actuator is less than the supplied reference action value by the minimum deficit of the control action candidates below the supplied reference action value;
    rule 3: if the control action candidates for an actuator do not meet the conditions for activating either rule 1 or rule 2, then the composite action value is the supplied reference action value.

4. A method as claimed in claim 3, wherein the supplied reference action value for at least one actuator is zero.

5. A method as claimed in claim 3, wherein the supplied reference action value for at least one actuator is the action value which will move the actuator to a minimum cost state.

6. A method as claimed in claim 1, wherein the control action is formed using control action candidate averaging.

7. A method as claimed in claim 6, wherein the averaging is weighted averaging.

8. A method as claimed in claim 1, wherein the control action is formed by selecting one control action from the control action candidates.

9. A method as claimed in claim 8, wherein the selected control action is the control action candidate which has the smallest 2-norm or smallest infinity norm of all the control action candidates.

10. A method as claimed in claim 1, wherein the desired values are predefined set points.

11. A method as claimed in claim 1, wherein plural perturbed process models are formed from a nominal process model and a supplied set of perturbations.

12. A method as claimed in claim 1, wherein at least one perturbed process model has been perturbed by a random amount.

13. A method as claimed in claim 1, wherein at least two process models have different model structures.

14. A method as claimed in claim 1, wherein the method is used in a multivariable control.

15. A method as claimed in claim 1, wherein the method is used in cross-directional control.

16. A method as claimed in claim 1, wherein the method is used in control of a spectroscopically measured quantity.

17. A control arrangement for controlling a sheet-making process, which is adapted to make a sheet matching desired values, which arrangement comprises:
    a measuring unit for measuring the state of the process, whereby one or more measurement value representing the state of the process is obtained;
    a comparator for comparing each measurement value with a corresponding desired value and for forming an error representing the difference between at least one measurement value and its desired value;
    a control unit adapted to utilize at least two process models, of which at least one is a perturbed model, and to form at least two control action candidates based on the error;
    a processing unit for forming one control action of the control action candidates, with which control action the control arrangement is adapted to control the sheet-making process to produce a sheet matching the desired values.

18. An arrangement as claimed in claim 17, wherein the processing unit is adapted to form the control action using rule-based composition of control action candidates.

19. An arrangement as claimed in claim 18, wherein the rule-based composition employs the following three rules:
    rule 1: if all control action candidates for an actuator exceed a supplied reference action value for the actuator, then a composite action value for the actuator exceeds the reference action value by the minimum excess of the control action candidates above the reference action value;
    rule 2: if all control action candidates for an actuator are less than a supplied reference value for the actuator, then the composite action value for the actuator is less than the supplied reference action value by the minimum deficit of the control action candidates below the supplied reference action value;
    rule 3: if the control action candidates for an actuator do not meet the conditions for activating either rule 1 or rule 2, then the composite action value is the supplied reference action value.

20. An arrangement as claimed in claim 19, wherein the supplied reference action value for at least one actuator is zero.

21. An arrangement as claimed in claim 20, wherein the supplied reference action value for at least one actuator is the action value which will move the actuator to a minimum cost state.

22. An arrangement as claimed in claim 17, wherein the processing unit is adapted to form the control action using control action candidate averaging.

23. An arrangement as claimed in claim 22, wherein the averaging is a weighted averaging.

24. An arrangement as claimed in claim 17, wherein the processing unit is adapted to select one control action from the control action candidates.

25. An arrangement as claimed in claim 24, wherein the selected control action is the control action candidate which has the smallest 2-norm or smallest infinity norm of all the control action candidates.

26. An arrangement as claimed in claim 17, wherein the desired values are predefined set points.

27. An arrangement as claimed in claim 17, wherein the processing unit is adapted to form plural perturbed process models from a nominal process model and a supplied set of perturbation amounts.

28. An arrangement as claimed in claim 17, wherein the processing unit has been adapted to form at least one perturbed process model using a random or pseudo-random perturbation amount.

29. An arrangement as claimed in claim 17, wherein at least two process models have different model structures.

30. An arrangement as claimed in claim 17, wherein the control arrangement is used in a multivariable control.

31. An arrangement as claimed in claim 17, wherein the control arrangement is used in cross-directional control.

32. An arrangement as claimed in claim 17, wherein the control arrangement is used in control of a spectroscopically measured quantity.

* * * * *

UNITED STATES PATENT AND TRADEMARK OFFICE
CERTIFICATE OF CORRECTION

PATENT NO. : 6,421,575 B1
DATED : July 16, 2002
INVENTOR(S) : Shakespeare

It is certified that error appears in the above-identified patent and that said Letters Patent is hereby corrected as shown below:

<u>Title page,</u>
Item [56], References Cited, U.S. PATENT DOCUMENTS, insert the following:
-- 4,893,262   1/1990      Kalata
5,122,963     6/1992      Chen
5,402,333     3/1995      Cardner --.
OTHER PUBLICATIONS, after "Journal" insert a comma (,) and a space.

Signed and Sealed this

Twelfth Day of November, 2002

*Attest:*

*Attesting Officer*

JAMES E. ROGAN
*Director of the United States Patent and Trademark Office*